United States Patent
Weinberger

(10) Patent No.: US 6,977,370 B1
(45) Date of Patent: Dec. 20, 2005

(54) OFF-RESONANCE MID-IR LASER DESORPTION IONIZATION

(75) Inventor: Scot R. Weinberger, Montara, CA (US)

(73) Assignee: Ciphergen Biosystems, Inc., Fremont, CA (US)

(*) Notice: Subject to any disclaimer, the term of this patent is extended or adjusted under 35 U.S.C. 154(b) by 39 days.

(21) Appl. No.: 10/804,723

(22) Filed: Mar. 19, 2004

Related U.S. Application Data

(60) Provisional application No. 60/462,419, filed on Apr. 9, 2003, provisional application No. 60/461,581, filed on Apr. 7, 2003.

(51) Int. Cl.[7] .................. G01N 33/50; G01N 33/48
(52) U.S. Cl. .................. 250/282; 288/423 P; 435/4; 435/6; 436/43; 436/86; 436/94; 436/173; 436/174
(58) Field of Search .................. 250/282, 288, 250/423 P; 436/43, 86, 94, 173, 174; 435/4, 435/6

(56) References Cited

U.S. PATENT DOCUMENTS

| | | | |
|---|---|---|---|
| 5,045,694 A | | 9/1991 | Beavis et al. |
| 5,118,937 A | | 6/1992 | Hillencamp et al. |
| 5,719,060 A | * | 2/1998 | Hutchens et al. ........... 436/174 |
| 6,225,047 B1 | | 5/2001 | Hutchens |
| 6,342,393 B1 | * | 1/2002 | Hofstadler et al. ......... 436/173 |
| 6,451,616 B1 | * | 9/2002 | Odom et al. ................ 436/173 |
| 6,558,902 B1 | * | 5/2003 | Hillenkamp ................... 435/6 |
| 6,656,690 B2 | * | 12/2003 | Crooke et al. ................. 435/6 |
| 6,683,300 B2 | * | 1/2004 | Doroshenko et al. ....... 250/288 |
| 6,706,530 B2 | * | 3/2004 | Hillenkamp .................. 436/94 |
| 6,723,564 B2 | * | 4/2004 | Hillenkamp .................. 436/94 |
| 2002/0138208 A1 | | 9/2002 | Paulse et al. |
| 2002/0193950 A1 | | 12/2002 | Gavin et al. |
| 2003/0004402 A1 | | 1/2003 | Hitt et al. |
| 2003/0032043 A1 | | 2/2003 | Pohl et al. |
| 2003/0055615 A1 | | 3/2003 | Zhang et al. |
| 2003/0124371 A1 | | 7/2003 | Um et al. |
| 2003/0148528 A1 | * | 8/2003 | Hillenkamp .................. 436/43 |
| 2003/0207460 A1 | | 11/2003 | Kitagawa |
| 2003/0228700 A1 | * | 12/2003 | Peters et al. .................. 436/86 |
| 2004/0007666 A1 | * | 1/2004 | Griffey et al. ............... 250/282 |
| 2004/0173740 A1 | * | 9/2004 | McLuckey et al. ......... 250/288 |

FOREIGN PATENT DOCUMENTS

| | | |
|---|---|---|
| WO | WO 00/66265 | 11/2000 |
| WO | WO 00/67293 | 11/2000 |
| WO | WO 01/31580 | 5/2001 |

OTHER PUBLICATIONS

J.W. Gauthier et al., "Sustained off-resonance irradiation for collision-activated dissociaton involving Fourier transform mass spectrormetry; Collision-activated dissociation technique . . . ", Anal. Chim. Acta 246 (1991) 211-225.*

(Continued)

*Primary Examiner*—John R. Lee
*Assistant Examiner*—Bernard E. Souw
(74) *Attorney, Agent, or Firm*—Fish & Neave IP Group Ropes & Gray LLP; James F. Haley, Jr.; Tae Bum Shin

(57) ABSTRACT

Methods for producing a preponderance of gas phase ions having higher order charge states during laser desorption ionization of an analyte are presented, the methods comprising irradiating the analyte in the presence of energy absorbing molecules at a mid-IR wavelength that is offset from an IR absorption maximum of the energy absorbing molecules.

28 Claims, 3 Drawing Sheets

OTHER PUBLICATIONS

Adam et al., "Serum Protein Fingerprinting Coupled with a Pattern-matching Algorithm Distinguishes Prostate Cancer from Benign Prostate Hyperplasia and Healthy Men," *Cancer Research*, 62:3609-3614 (2002).

Ball et al., "An Integrated Approach Utilizing Artificial Neural Networks and SELDI Mass Spectrometry for the Classification of Human Tumours and Rapid Identification of Potential Biomarkers," *Bioinformatics*, 18(3):395-404 (2002).

Jain, "Statistical Pattern Recognition: A Review", IEEE Transactions on Pattern Analysis and Machine Intelligence, vol. 22, No. 1, Jan. 2000.

Li et al., "Proteomics and Bioinformatice Approaches for Identification of Serum Biomarkers to Detect Breast Cancer," *Clinical Chemistry Journal*, 48:1296-1304 (2002).

Petricoin et al., "Use of Proteomic Patterns in Serum to Identify Ovarian Cancer," *The Lancet*, 359:572-577 (2002).

Rai et al., "Proteomic Approaches to Tumor Marker Discovery; Identification of Biomarkers for Ovarian Cancer," *Archives of Pathology and Laboratory Medicine*, 126: 1518-1526 (2002).

* cited by examiner

OFF-RESONANCE MID-IR LASER DESORPTION IONIZATION

CROSS REFERENCE TO RELATED APPLICATIONS

This application claims the benefit of U.S. provisional application Nos. 60/462,419, filed Apr. 9, 2003 and 60/461,581, filed Apr. 7, 2003, the disclosures of which are incorporated herein by reference in their entireties.

FIELD OF THE INVENTION

The present invention is in the field of gas phase ion spectrometry, and is particularly related to methods for laser desorption ionization of mass spectral analytes.

BACKGROUND OF THE INVENTION

Over the past decade, laser desorption ionization (LDI) techniques, including matrix-assisted laser desorption ionization (MALDI) and surface-enhanced laser desorption ionization (SELDI), have revolutionized the mass spectral analysis of large analytes, including biomolecules. In particular, the recent marriage of LDI sources to a variety of improved tandem (MS/MS) mass spectrometers has significantly expedited protein discovery and characterization.

Certain operational limits currently constrain the usefulness of tandem mass spectrometers in such analyses, however.

For example, collision-induced dissociation (CID) and product ion scans are typically limited to ions having a mass-to-charge (m/z) ratio of no more than about 5000. This limit is attributable in part to constraints on the ability to select precursor ions for CID with adequate resolution, to constraints on the amount of energy that can be delivered to the selected ion, and to stochastic constraints on proton availability to promote fragmentation of the selected ions. This m/z limitation applies to virtually every current tandem mass spectrometer instrument type, including quadrupole time-of-flight (QqTOF), triple quadrupole, ion trap, ion trap time-of-flight, time-of-flight/time-of-flight (TOF/TOF), and ion cyclotron resonance (ICR) mass spectrometers.

The m/z limit for CID and product ion scans particularly constrains tandem MS analysis of singly charged ions, since the unitary charge limits analysis to ions having a mass of no more than about 5000 daltons.

Current MALDI and SELDI ion sources using ultraviolet lasers at 337 nm typically generate a predominance of unit charge molecular ions, often to the exclusion of ions with higher order charge states, thus constraining the ability to use MALDI and SELDI ion sources for tandem MS applications.

Hillencamp et al., U.S. Pat. No. 5,118,937, teach that an increase in incident laser wavelength from 266 nm to greater than about 300 nm, including an increase to IR wavelengths of 3.0–10.6 μm, advantageously decreases analyte absorption of laser irradiation during matrix-assisted laser desorption ionization.

Hillencamp et al. also teach in general terms that certain combinations of IR wavelength and IR matrix produce ions with higher numbers of charges, and notes that such higher order charge states improve collisional and photon bombardment fragmentation in tandem MS applications. The patent does not, however, disclose with specificity which combinations of wavelength and matrix achieve this effect and does not disclose a method for choosing such combinations, although the patent suggests that IR-effective matrices should be chosen to exhibit strong absorption at the chosen wavelength.

There thus exists a need in the art for laser desorption ionization methods that produce a preponderance of gas phase ions having higher order charge states, particularly for use in tandem mass spectral analyses. There also exists a need for methods of choosing combinations of energy absorbing molecules, such as MALDI matrices, and laser wavelengths that lead to a preponderance of ions having higher order charge states during laser desorption ionization of mass spectral analytes.

SUMMARY OF THE INVENTION

The present invention solves these and other needs in the art by providing, in a first aspect, a method for producing a preponderance of gas phase ions having higher order charge states during laser desorption ionization of an analyte. The method comprises irradiating the analyte in the presence of energy absorbing molecules at a mid-IR wavelength that is offset from an IR absorption maximum of the energy absorbing molecules.

The analyte may be within a matrix of the energy absorbing molecules. Alternatively, the energy absorbing molecules may be photoactive components of a surface upon which the analyte is disposed. The mid-IR wavelength may be produced by a fixed wavelength laser or by a tunable laser, such as a tunable optical parametric oscillator (OPO) infrared laser.

In various embodiments, the method may further comprise the subsequent step of detecting at least a plurality of the higher order charge state gas phase ions; detecting may be performed using an ion mobility spectrometer, a total ion current measuring device, or a mass spectrometer. In embodiments in which detection is by a mass spectrometer, the method further includes a mass spectral analysis.

In embodiments in which detection is by a tandem mass spectrometer, the mass spectral analysis may be a tandem mass spectral analysis.

The tandem mass spectrometer may be selected from the group consisting of QqTOF mass spectrometer, triple quadrupole mass spectrometer, ion trap mass spectrometer, ion trap time-of-flight (TOF) mass spectrometer, ion cyclotron resonance (ICR) mass spectrometer, time-of-flight time-of-flight (TOF-TOF) mass spectrometer, Fourier transform ion cyclotron resonance mass spectrometer, electric sector-magnetic sector mass spectrometer, magnetic sector-electric sector mass spectrometer, and electric sector-electric sector mass spectrometer.

In certain embodiments, the tandem mass spectral analysis comprises: selecting at least a first ion species; fragmenting the at least first ion species into a plurality of product ion species; and then performing a mass spectral analysis on at least one of the product ion species. Fragmentation may be by a spontaneous unimolecular process, such as in-source or post-source decay, or may be induced by known ion activation methods, including collision induced dissociation, surface-induced dissociation, photodissociation, or electron-induced dissociation, with collision induced dissociation typically preferred.

In such tandem MS analyses, the selected first ion species may have a mass greater than about 5000 daltons, 10,000 daltons, 15,000 daltons, even 25 kDal.

In various embodiments, the tandem mass spectral analysis may comprise a product ion scan of the product ions.

The method of the present invention may further comprise the antecedent step of adsorbing the analyte from an inhomogeneous sample directly onto a SELDI probe, which may be a SEND probe. The method may further comprise the step, after adsorbing and before irradiating the analyte, of contacting the probe-adsorbed analyte with energy absorbing molecules.

The analyte may be any analyte desired to be analyzed.

In one series of embodiments, the analyte is usefully a protein.

In certain of the embodiments of the methods of the present invention in which the analyte is a protein, the method may further comprise a later step of determining at least a partial amino acid sequence of the protein analyte. The partial amino acid sequence may, for example, be determined at least in part by calculating differences in masses among product ions represented in a product ion scan. The partial amino acid sequence can be used, in various embodiments, to identify the protein analyte by querying a database with at least a portion of the at least partial protein sequence.

In an alternative, the protein analyte may be identified without partial sequencing, by comparing a product ion scan of the protein analyte to product ion scans predicted from protein or nucleic acid sequence databases, and then using the most similar predicted product ion scan to identify said protein analyte.

In another aspect, the invention provides a method of choosing EAMs that are capable, at a given mid-IR wavelength, of producing a preponderance of gas phase ions having higher order charge states during laser desorption ionization of an analyte. The method comprises identifying an EAM with a mid-IR absorption maximum offset from the given mid-IR wavelength, and then testing the EAM at that wavelength for its ability to produce a preponderance of gas phase ions having higher order charge states during laser desorption ionization of an analyte.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which.

DETAILED DESCRIPTION OF THE INVENTION

Figure 1A:
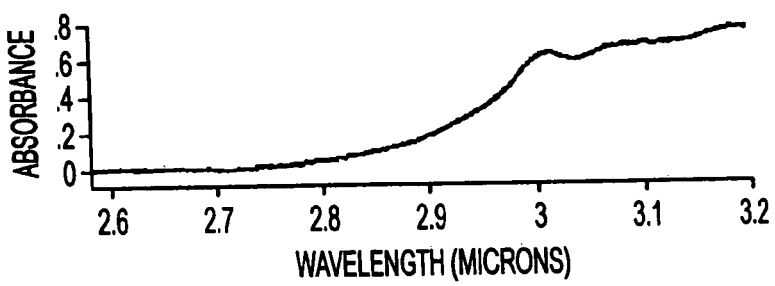
FIGS. 1A–1E show IR absorbance spectra of five known MALDI matrices (A: 2,5-dihydroxybenzoic acid; B: α-cyano-4-hydroxycinnamic acid; C: sinapinic acid; D: ferulic acid; and E: caffeic acid), as described in the prior art.
Figure 1B:
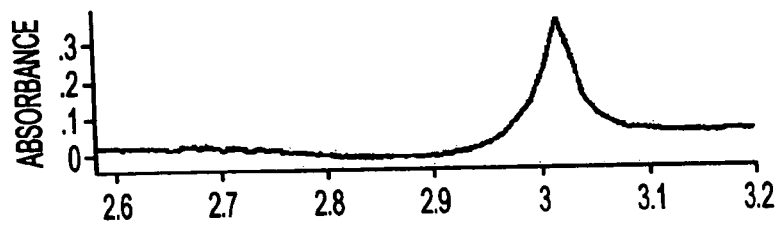
Figure 1C:
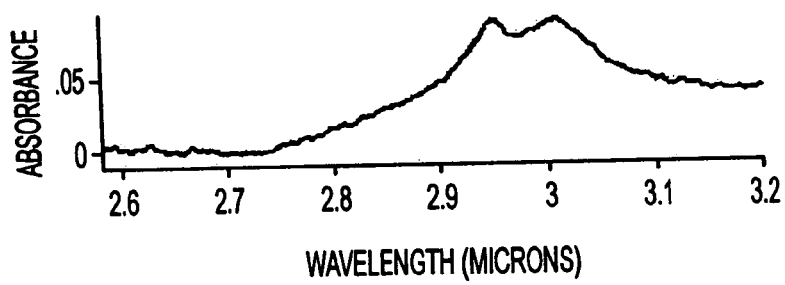
Figure 1D:
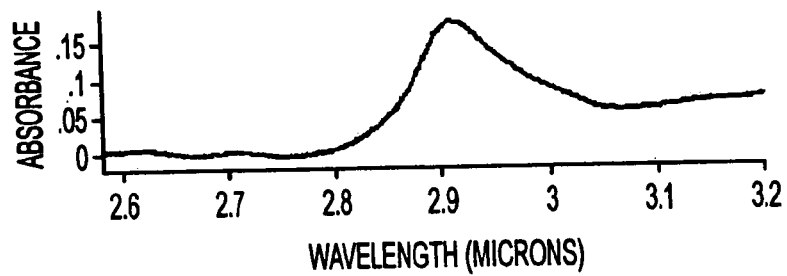

In a first aspect, the invention provides a method for producing a preponderance of gas phase ions having higher order charge states during laser desorption ionization of an analyte. By increasing the proportion of higher charge state ions, the method is capable of significantly and advantageously expanding the mass range of MSMS analysis well beyond the current functional limit of about 5000 daltons.

The method comprises irradiating the analyte, in the presence of energy absorbing molecules, at a mid-IR wavelength that is offset from an IR absorption maximum of the energy absorbing molecules.

As used herein, "analyte" refers to any component of a sample that is desired to be detected and optionally analyzed. The term can refer to a single component or to a plurality of components in the sample.

Among the analytes that can usefully be desorbed and ionized according to the methods of the present invention are biomolecules derived from archaea, eubacteria, or eukaryotes. The biomolecules can usefully be polymers, such as proteins, nucleic acids, lipids, and oligosaccharides. By "proteins" is intended any size of amino acid polymer, and the term thus explicitly comprehends peptides, oligopeptides, and polypeptides. Similarly, the phrase "nucleic acids" comprises any size of nucleotide polymer, and thus explicitly comprehends oligonucleotides and polynucleotides; the phrase "oligosaccharides" comprises any size saccharide polymer, including both linear and branched saccharide polymers; and the term lipids includes any size lipid.

The analyte is typically disposed upon a probe in the presence of energy absorbing molecules.

In the context of this invention, "probe" refers to a device adapted to engage a probe interface of a gas phase ion spectrometer and to present an analyte to ionizing energy for ionization and introduction into a gas phase ion spectrometer. A "probe" will generally comprise a solid substrate (either flexible or rigid) comprising a sample presenting surface on which an analyte is presented to the source of ionizing energy.

The phrase "energy absorbing molecules" ("EAM") refers to molecules that are capable of absorbing energy from a laser desorption/ionization source and thereafter contributing to desorption and ionization of analyte molecules in contact therewith.

The phrase thus includes molecules used in UV and IR MALDI, frequently referred to as "matrix", and explicitly includes cinnamic acid derivatives, sinapinic acid ("SPA"), cyano-hydroxy-cinnamic acid ("CHCA"), dihydroxybenzoic acid, ferulic acid, caffeic acid, hydroxyacetophenone derivatives, water, glycerol, water/glycerol mixtures, frozen alcohol, DHB, succinic acid, urea, as well as others.

EAM also include energy absorbing molecules used in SELDI and SEND, and accordingly, the probes can be SELDI or SEND probes.

SELDI ("surface-enhanced laser desorption/ionization") refers, in one series of embodiments, to a method of desorption/ionization gas phase ion spectrometry (e.g., mass spectrometry) in which the analyte is captured on the surface of a SELDI probe that engages the probe interface of a gas phase ion spectrometer. In "SELDI MS," the gas phase ion spectrometer is a mass spectrometer. SELDI technology is described, e.g., in U.S. Pat. Nos. 5,719,060 and 6,225,047, the disclosures of which are incorporated herein by reference in their entireties.

SEND ("Surface-Enhanced for Neat Desorption") is a version of surface-enhanced laser desorption ionization that involves the use of probes comprising energy absorbing molecules chemically bound to the probe surface. SEND is further described in U.S. Pat. No. 5,719,060, which is incorporated herein by reference in its entirety.

Newer SEND surfaces, described in commonly owned U.S. patent application Ser. No. 10/326,219, filed Dec. 20, 2002 and incorporated herein by reference in its entirety, include matrices polymerized from monomers that include a polymerizable moiety and a photoreactive group. The resulting polymers are photoreactive, and thus absorb photo-irradiation from a high fluence source to generate thermal energy, and act to transfer the thermal energy to allow desorption and ionization of the analyte molecules.

In one series of embodiments, the polymeric material is a homopolymer (optionally cross-linked) made from monomers comprising a moiety that absorbs the photo-irradiation and a polymerizable moiety such as a vinyl group or a methacryl group. In another series of embodiments, the photo-reactive polymer is a heteropolymer (optionally cross-linked) comprising photo-reactive monomers and monomers comprising binding functionalities. In another series of embodiments, the polymeric material comprises a photo-reactive polymer and a polymer derivatized with binding functionalities.

For purposes of the methods of the present invention, the photoreactive group will be sufficiently absorptive in the mid-IR range as to allow the polymer to function as EAM for laser desorption ionization upon mid-IR irradiation. As with other types of EAM useful in the methods of the present invention, such photoreactive groups may absorb principally in the infrared, or may additionally have absorption maxima in the UV range.

In one series of embodiments, the photoreactive group may usefully include an aryl nucleus having a substituent thereon. The substituent may include a carbonyl or carboxyl group that is electronically conjugated to the π-system of the aryl nucleus. In certain exemplary embodiments, the monomers of the invention have a structure such as that set forth below:

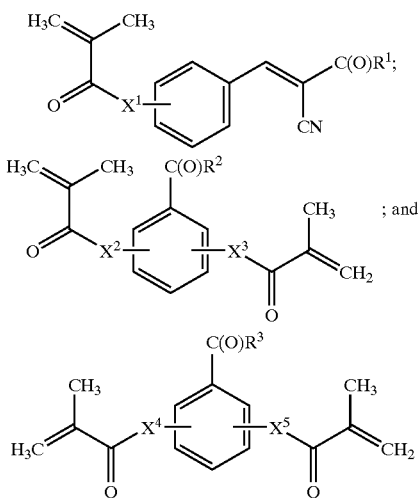

in which the symbols $R^1$, $R^2$ and $R^3$ represent members independently selected from H, $NR^4R^5$, $OR^6$, substituted or unsubstituted alkyl, substituted or unsubstituted heteroalkyl and substituted or unsubstituted aryl. The symbols $X^1$, $X^2$ and $X^3$ represent members independently selected from the group consisting of O, $NR^7R^8$ and S. The symbols $R^4$, $R^5$, $R^6$, $R^7$, and $R^8$ represent members independently selected from the group consisting of H, substituted or unsubstituted alkyl, substituted or unsubstituted heteroalkyl and substituted or unsubstituted aryl.

In particularly useful embodiments, the polymerizable monomer is α-cyano-4-methacryloyloxycinnamic acid, 2,5-dimethacryloyloxybenzoic acid or 2,6-dimethacryloyloxyacetophenone. In one such embodiment, the SEND EAM may be a co-polymer of α-cyano-4-methacryloyloxycinnamic acid and acrylate. In another embodiment, the SEND EAM composition may be a co-polymer of α-cyano-4-methacryloyloxycinnamic acid, acrylate and 3-(tri-methoxy) silyl propyl methacrylate. In yet a further embodiment, the SEND EAM composition is a co-polymer of α-cyano-4-methacryloyloxycinnamic acid and octadecylmethacrylate.

The polymer matrix is readily prepared by art-recognized polymerization methods. For example, a solution of the monomer can be deposited onto the probe and subsequently polymerized or, alternatively, the monomer can be polymerized and the resulting polymer deposited onto the probe. The matrix can be a homopolymer of the EAM, a mixture of more than one EAM, or a mixture of one or more EAM and a monomer having a desired property (e.g., a desired charge, degree of hydrophilicity, or degree of hydrophobicity). Thus, it is possible to "tune" the properties of the matrix by varying the nature and concentration of the constituents of the polymeric matrix. In addition to the chemical properties, the morphology of the polymer can be varied as well. For example, the polymer can be a film or it can be formed under suspension or emulsion polymerization conditions to form beads or particles of the matrix. Moreover, the polymer can be made nonporous, microporous, or macroporous materials by means of porogens.

The properties of the SEND EAM polymer matrix can be tuned by varying the structure of the monomers utilized in forming the polymeric matrix. For example, the concentration of EAMs within the matrix can be varied to provide the appropriate density of energy-absorbing molecules bonded (covalently or noncovalently) such that the energy-absorbing molecules can be used to facilitate the desorption of analyte molecules of varying masses. The optimum ratio of adsorbed or bonded energy-absorbing molecules to analyte generally varies with the mass of the analyte to be detected. Moreover, the energy absorbing molecules within the polymer matrix may be combined with affinity reagents, chemical and/or biological, for the specific purpose of capturing (adsorbing) specific analyte molecules or classes of analyte molecules for the subsequent preparation, modification, and desorption of the analyte molecules.

Accordingly, in certain embodiments of the methods of the present invention the energy absorbing molecules may embed the analyte, as in a MALDI matrix or certain applications of the polymeric EAM described above; in other embodiments, the energy absorbing molecules can be photoactive components of a surface upon which the analyte is disposed.

Among SELDI and SEND probes that may usefully be employed in the practice of the methods of the present invention are those having chromatographic or biospecific adsorbents attached thereto at addressable locations, such as the NP20, H4, H50, SAX-2, WCX-2, CM-10, IMAC-3, IMAC-30, LSAX-30, LWCX-30, IMAC-40, PS-10, PS-20 and PG-20 Ciphergen ProteinChip® arrays (Ciphergen Biosystems, Inc., Fremont, Calif., USA).

The ProteinChip® arrays comprise an aluminum substrate in the form of a strip. The surface of the strip is coated with silicon dioxide.

In the case of the NP-20 ProteinChip® array, silicon oxide functions as a hydrophilic adsorbent to capture hydrophilic proteins.

H4, H50, SAX-2, WCX-2, CM-10, IMAC-3, IMAC-30, PS-10 and PS-20 ProteinChip® arrays further comprise a functionalized, cross-linked polymer in the form of a hydrogel physically attached to the surface of the biochip or covalently attached through a silane to the surface of the probe.

The H4 ProteinChip® array has isopropyl functionalities for hydrophobic binding. The H50 ProteinChip® array has nonylphenoxy-poly(ethylene glycol)methacrylate for hydrophobic binding. The SAX-2 ProteinChip® array has quaternary ammonium functionalities for anion exchange. The WCX-2 and CM-10 ProteinChip® arrays have carboxylate functionalities for cation exchange. The IMAC-3 and IMAC-30 ProteinChip® arrays have nitriloacetic acid functionalities that adsorb transition metal ions, such as $Cu^{++}$ and $Ni^{++}$, by chelation. These immobilized metal ions allow adsorption of peptide and proteins by coordinate bonding. The PS-10 ProteinChip® array has carboimidizole functional groups that can react with groups on proteins for covalent binding. The PS-20 ProteinChip® array has epoxide functional groups for covalent binding with proteins. The PS-series ProteinChip® arrays are useful for binding biospecific adsorbents, such as antibodies, receptors, lectins, heparin, Protein A, biotin/streptavidin and the like, to probe surfaces where they function to specifically capture analytes from a sample. The PG-20 ProteinChip® array is a PS-20 ProteinChip® to which Protein G is attached. The LSAX-30 (anion exchange), LWCX-30 (cation exchange) and IMAC-40 (metal chelate) ProteinChip® have functionalized latex beads on their surfaces. Such ProteinChip® arrays are further described in: WO 00/66265, WO 00/67293, U.S. patent application publication U.S. 2003/0032043A1, and U.S. patent application 60/350,110, the disclosures of which are incorporated herein by reference in their entireties.

The analyte, in the presence of energy absorbing molecules, is desorbed and ionized at a mid-IR wavelength.

As used herein, "mid-IR" wavelengths are wavelengths from 2.5–3.5 µm, inclusive, and thus include wavelengths as low as 2.5, 2.6, 2.7, 2.8, 2.9, even 3.0 µm, and wavelengths as high as 3.5, 3.4, 3.3, 3.2, even 3.1 µm, as well as any wavelengths within the spectrum from 2.5–3.5 µm.

Infrared lasers capable of emitting in the mid-IR range are well known in the art, and can be either fixed wavelength lasers, such as Er:YAG lasers ($\lambda=2.94$ µm), or tunable lasers, such as an optical parametric oscillator (OPO) lasers ($\lambda=2.8-3.3$ µm). Tunable lasers advantageously allow the desorption/ionization wavelength to be adjusted without requiring a change in the laser source itself.

IR laser desorption ionization is known, and the "softness" of IR desorption ionization is known to provide advantages in the laser desorption ionization of fragile biomolecules. Another known advantage is the wider variety of energy absorbing molecules, typically as MALDI matrices, that can be used in the IR as compared to UV spectrum, with the availability of IR-absorbing liquid matrices providing the potential for direct interface with upstream liquid separations techniques.

Given the lower energies imparted by IR irradiation as compared to UV wavelengths, however, wavelengths preferred for IR LDI have typically been chosen to approximate as closely as practicable the absorption maxima (resonance wavelengths) of the energy absorbing molecules.

In the methods of the present invention, by contrast, the mid-IR wavelength chosen for desorption/ionization of the analyte is offset from an IR absorption maximum of the energy absorbing molecules. Surprisingly, such offset leads to the generation of increased numbers of gas phase ions with higher order charge states.

IR absorption maxima of energy absorbing molecules can be determined from their IR absorption spectra.

IR absorption spectra, and methods for generating them, are well known. For example, FIGS. 1A–1E present IR absorption spectra that have previously been published for five common MALDI matrices. Spectra for other EAM, if not available in the published literature, can readily be produced using, e.g., standard infrared or Fourier transform infrared (FT-IR) spectroscopy, or other known analytical techniques.

The degree of offset from an EAM IR absorption maximum is chosen to produce, for at least one species of analyte-derived ion, a preponderance of higher order charge state ions.

By "preponderance" is here intended that one or more of the higher order charge states exceeds in abundance the respective singly charged (i.e., unit charge, or true molecular) ion. Higher order charge states include, e.g., +2, +3, +4, +5, even +6 or more for positive ions, and –2, –3, –4, –5, even –6 or more for negative ions.

"Preponderance" includes both "true preponderance" and "observed preponderance".

By "true preponderance" is intended that one or more of the higher order charge states of any one or more of the ions having mass from 2,000 daltons–10,000 daltons exceeds in abundance its respective singly charged ion, as measured using a detector having isotopic resolution.

Since many of the advantageous uses of the methods of the present invention will be found in gas phase ion spectrometers that may lack such isotopic resolution, however, the method also provides, in certain embodiments, a preponderance of gas phase ions with higher order charge states as detected using the spectrometer with which the laser desorption ion source directly communicates ("observed preponderance"). When the gas phase ion spectrometer with which the laser desorption ion source directly communicates has isotopic resolution, the observed preponderance may be a true preponderance.

As used herein, "gas phase ion spectrometer" refers to an apparatus that detects gas phase ions. Gas phase ion spectrometers include, for example, mass spectrometers, ion mobility spectrometers, and total ion current measuring devices.

"Mass spectrometer" refers to a gas phase ion spectrometer that measures a parameter that can be translated into mass-to-charge ratios of gas phase ions. Mass spectrometers generally include an ion source and a mass analyzer. Examples of mass spectrometers are time-of-flight, magnetic sector, quadrupole filter, ion trap, ion cyclotron resonance, electrostatic sector analyzer and hybrids thereof.

"Tandem mass spectrometer" refers to any mass spectrometer that is capable of performing two successive stages of m/z-based discrimination or measurement of ions, including ions in an ion mixture. The phrase includes mass spectrometers having two mass analyzers that are capable of performing two successive stages of m/z-based discrimination or measurement of ions tandem-in-space. The phrase further includes mass spectrometers having a single mass analyzer that is capable of performing two successive stages of m/z-based discrimination or measurement of ions tandem-in-time. The phrase thus explicitly includes Qq-TOF mass spectrometers, ion trap mass spectrometers, ion trap-TOF mass spectrometers, TOF-TOF mass spectrometers, Fourier transform ion cyclotron resonance mass spectrometers, electrostatic sector—magnetic sector mass spectrometers, and combinations thereof.

For any given species of EAM, the degree of offset required to produce a preponderance of gas phase ions having higher order charge states can be determined empirically.

For example, a test analyte, such as human ACTH, can be prepared for laser desorption ionization on one or more probes in the presence of the desired EAM species using known techniques. A mass spectrum is then obtained by standard techniques at or near a mid-IR absorption maximum of the EAM. One or more additional mass spectra are obtained at wavelengths variously offset from the mid-IR absorption maximum of the EAM, in either or both directions on the spectrum (i.e., toward shorter wavelengths or longer wavelengths). The abundance of higher order charge states, normalized to the abundance of a respective singly charged species, is then compared to identify an off-resonance mid-IR wavelength providing an observed preponderance of higher charge state ions.

The process can optionally be iterated to identify a wavelength that provides the greatest percentage of higher order charge state ions, or to identify one or more wavelengths that provide a preponderance of a desired charge state, such as +2, +3, etc.

Conversely, for any given mid-IR wavelength, a matrix (or other EAM, such as EAM for SEND applications) may be selected empirically that has an absorption maximum sufficiently offset from a chosen wavelength to produce a preponderance of gas phase ions having higher order charge states.

Typically, once a preponderance of higher charge state gas phase ions has been generated according to the methods of the present invention, at least one species thereof is detected, and optionally analyzed, using a gas phase spectrometer, such as an ion mobility spectrometer, a total ion current measuring device, or a mass spectrometer.

The methods prove particularly useful in conjunction with subsequent detection by a mass spectrometer, usefully a tandem mass spectrometer, such as a tandem mass spectrometer selected from the group consisting of QqTOF mass spectrometer, ion trap mass spectrometer, ion trap time-of-flight (TOF) mass spectrometer, time-of-flight time-of-flight (TOF-TOF) mass spectrometer, and Fourier transform ion cyclotron resonance mass spectrometer.

Tandem mass spectral detection and analysis may, in some embodiments, comprise selecting at least a first ion species, fragmenting the selected ion species into a plurality of product ion species, and then performing a mass spectral analysis on at least one of the species of product ions.

Given the preponderance of higher order charge state ions, the ion selected for fragmentation may have a mass greater than about 5000 daltons. Depending upon the selection and fragmentation limitations of the tandem mass spectrometer and the charge state of the selected ion, the selected ion species may have a mass greater than about 7500 daltons, 10 kDal, 15 kDal, 20 kDal, 25 kDal, even 30 kDal or more.

Fragmentation may occur spontaneously by unimolecular decay, either as in-source or post-source decay, or may instead or in addition be created by any known ion activation method, including collision induced dissociation, surface-induced dissociation, photodissociation, or electron-induced dissociation, with collision induced dissociation typically preferred.

The tandem mass spectral analysis of the product ions may comprise, e.g., a product ion scan.

Detection and analysis may also be performed using a single stage of mass spectrometry, including a single stage performed in a tandem mass spectrometer. In such analyses, the generation of higher order charge state ions can increase sensitivity.

In embodiments of the methods of the present invention in which the analyte is protein, the methods of the present invention may usefully comprise a step of determining at least a partial amino acid sequence of the protein analyte. The sequence may be determined, at least in part, by calculating differences in masses among product ions detected in a product ion scan. The method may further comprise a later step of identifying the protein analyte by querying a protein sequence or nucleic acid sequence database using at least a portion of the protein sequence so determined as a query. Alternatively, the sequence may be determined by comparing the product ion scan to product ion scans predicted from protein or nucleic acid sequence databases.

In certain of the embodiments of the methods of the present invention in which the analyte is a protein, the methods of the present invention may further comprise later steps of protein profiling and/or difference mapping.

In protein profiling, a plurality of proteins derived from a sample are detected and analyzed, the mass spectrum of the plurality of protein analytes providing a "profile" of the proteins, or a subset of the proteins, present within the sample. In difference mapping, spectra, spectral peaks, and/or protein profiles are compared to categorize samples based upon the relative presence, absence, or abundance of proteins therein.

The large quantities of data obtained through protein profiling, difference mapping, protein sequencing, and protein identification, although capable of manual analysis, are usefully analyzed using digital computers programmed to store, analyze, and compare multidimensional datasets.

A computer can, e.g., transform the resulting spectrum into various formats for displaying. In one format, referred to as "spectrum view or retentate map," a standard spectral view can be displayed, wherein the view depicts the quantity of analyte reaching the detector at each particular molecular weight. In another format, referred to as "peak map," only the peak height and mass information are retained from the spectrum view, yielding a cleaner image and enabling analytes with nearly identical molecular weights to be more easily seen. In yet another format, referred to as "gel view," each mass from the peak view can be converted into a grayscale image based on the height of each peak, resulting in an appearance similar to bands on electrophoretic gels. In yet another format, referred to as "3-D overlays," several spectra can be overlaid to study subtle changes in relative peak heights. In yet another format, referred to as "difference map view," two or more spectra can be compared, conveniently highlighting unique analytes and analytes that are up- or down-regulated between samples.

Analysis generally involves the identification of peaks in the spectrum that represent signal from an analyte. Peak selection can be done by eye. Usefully, however, software can be used to automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Peak data from one or more spectra can be subject to further analysis by, for example, creating a spreadsheet in which each row represents a particular mass spectrum, each column represents a peak in the spectra defined by mass, and each cell includes the intensity of the peak in that particular spectrum. Various statistical or pattern recognition approaches can applied to the data.

The spectra that are generated in embodiments of the invention can be classified using a pattern recognition process that uses a classification model. In general, the spectra will represent samples from at least two different groups for which a classification algorithm is sought. For example, the groups can be pathological v. non-pathological (e.g., cancer v. non-cancer), drug responder v. drug non-responder, toxic response v. non-toxic response, progressor to disease state v. non-progressor to disease state, phenotypic condition present v. phenotypic condition absent.

In some embodiments, data derived from the spectra (e.g., mass spectra or time-of-flight spectra) that are generated using samples such as "known samples" can then be used to "train" a classification model. A "known sample" is a sample that is pre-classified. The data that are derived from the spectra and are used to form the classification model can be referred to as a "training data set". Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased vs. non-diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000.

In supervised classification, training data containing examples of known categories are presented to a learning mechanism, which learns one more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as backpropagation networks, discriminant analyses (e.g., Bayesian classifier or Fischer analysis), logistic classifiers, and support vector classifiers (support vector machines).

A useful supervised classification method is a recursive partitioning process. Recursive partitioning processes use recursive partitioning trees to classify spectra derived from unknown samples. Further details about recursive partitioning processes are in U.S. patent application publication 2002/0138208 A1 (Paulse et al., "Method for analyzing mass spectra," Sep. 26, 2002).

In other embodiments, the classification models that are created can be formed using unsupervised learning methods. Unsupervised classification attempts to learn classifications based on similarities in the training data set, without pre classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described in, for example, WO 01/31580 (Barnhill et al., "Methods and devices for identifying patterns in biological systems and methods of use thereof," May 3, 2001); U.S. patent application publication 2002/0193950 A1 (Gavin et al., "Method or analyzing mass spectra," Dec. 19, 2002); U.S. 2003/0004402 A1 (Hitt et al., "Process for discriminating between biological states based on hidden patterns from biological data," Jan. 2, 2003); U.S. 2003/0055615 A1 (Zhang and Zhang, "Systems and methods for processing biological expression data" Mar. 20, 2003).

The classification models can be formed on and used on any suitable digital computer. Suitable digital computers include micro, mini, or large computers using any standard or specialized operating system such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

Although particularly described herein with respect to protein analytes, the algorithmic approaches above-described prove useful with other types of analytes as well.

Examples of such analyses for biomarker discovery, disease diagnosis and disease classification (albeit using ultraviolet laser desorption ionization) are described, inter alia, in Rai et al., *Archives of Pathology and Laboratory Medicine,* 126:1518–1526, (2002); Li et al., *Clinical Chemistry Journal,* 48: 1296–1304 (2002); Adam et al., *Cancer Research* 62:3609–3614 (2002); Petricoin et al., *The Lancet,* 359: 572–577 (2002); Ball et al., *Bioinformatics,* 18(3): 395–404 (2002), the disclosures of which are incorporated herein by reference in their entireties.

The following example is offered by way of illustration only, and not by way of limitation.

EXAMPLE 1

Off-Resonance Mid-IR LDI of Proteins

UV-LDI at 337 nm is performed on both a Ciphergen linear TOF-MS (Ciphergen Biosystems, Inc., Fremont, Calif., USA), and an MDS-Sciex QStar® QqTOF tandem mass spectrometer (MDS Sciex, Concord, Ontario, Canada) equipped with a Ciphergen ProteinChip® Interface (Ciphergen Biosystems, Inc., Fremont, Calif., USA), both using a nitrogen laser (Spectra-Physics, Mountain View, Calif., USA) as laser source. All of the UV experiments are performed using CHCA (α-cyano-4-hydroxycinnamic acid) as the energy absorbing molecules.

Mid-IR (2.75 µm–3.00 µm) LDI experiments are performed on a custom-built, linear TOF-MS device, similar to the Ciphergen linear TOF-MS used for UV-LDI experiments, with a LaserVision tunable optical parametric oscillator (OPO) infrared laser (LaserVision, Bellevue, Wash., USA) providing off-resonance mid-IR light excitation. Mid-IR experiments are performed using caffeic acid as energy absorbing molecules.

Common high-molecular weight peptides and low-molecular weight proteins are used as test analytes to evaluate the efficiency with which multiply charged ions are formed using off-resonance mid-IR excitation.

Three biomolecules—human ACTH (4541 Da), bovine growth hormone releasing factor (5107 Da), and human parathyroid hormone (9424 Da)—are tested under the three conditions. These biomolecules are chosen (i) for their size, i.e. that their multiply charged ions could bring them into MSMS range on a typical tandem-MS device, and (ii) for their lack of disulfide bonds, in order to simplify the experimental variables.

Figure 1E:
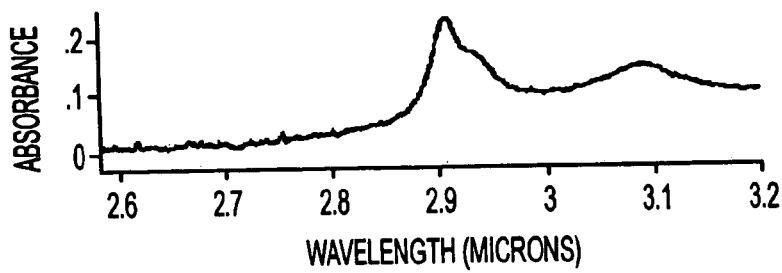
Figure 2A:
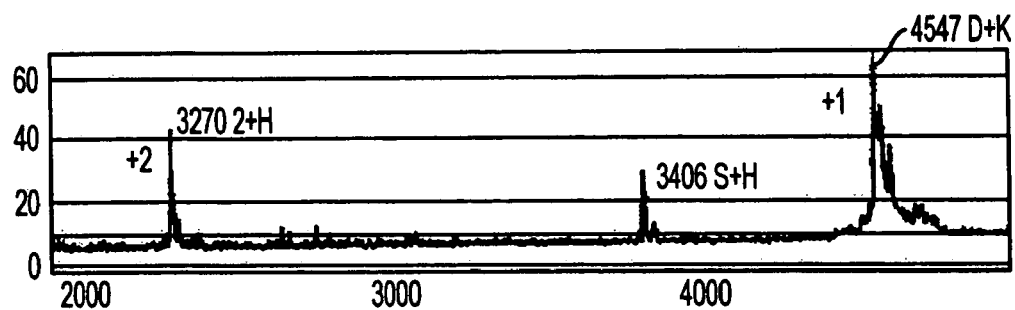
FIGS. 2A and 2B show mass spectra of a large peptide, adrenocorticotropin hormone (ACTH), obtained using prior art UV LDI at 337 nm on two devices, a linear TOF mass spectrometer (FIG. 2A) and QqTOF (FIG. 2B)
Figure 2B:
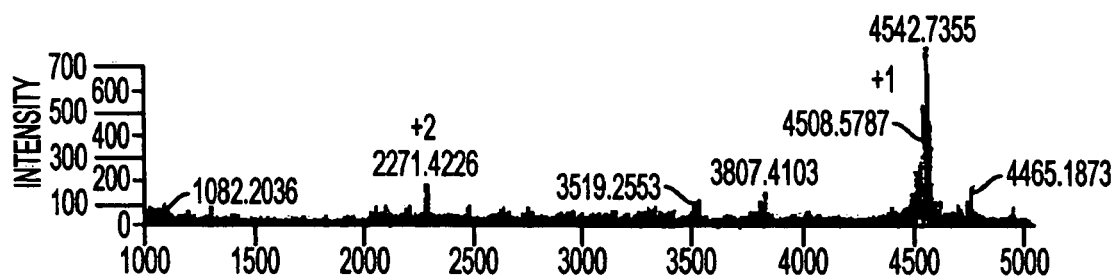
Figure 3:
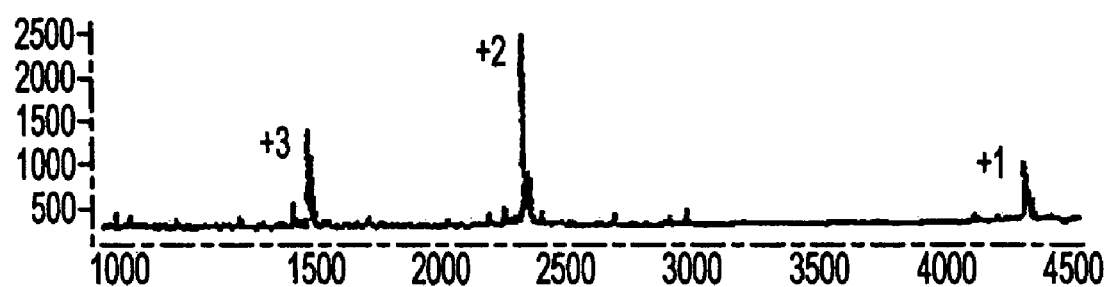
FIG. 3 shows the mass spectrum of ACTH on a linear TOF mass spectrometer obtained with off-resonance mid-IR LDI at 2.82 $\mu$m, according to the present invention, showing increased abundance of the +2 and +3 charge states as compared to UV LDI.

Exemplary results for ACTH are shown in FIGS. 2A, 2B, and 3, with FIGS. 2A and 2B respectively showing mass spectra of ACTH obtained using 337 nm UV-LDI in the linear TOF-MS (FIG. 2A) and QqTOF (FIG. 2B), and with FIG. 3 showing the mass spectrum of ACTH on the linear TOF mass spectrometer with mid-IR LDI at 2.82 µm. The 2.82 µm wavelength is an off-resonance wavelength: as shown in FIG. 1E, caffeic acid shows maximal IR absorbance above 2.9 µm.

Comparing FIGS. 3 to 2A and 2B demonstrates an increased abundance of the +2 and +3 charge states using off-resonance mid-IR LDI as compared to UV LDI.

The percentages of the +2 charge state of ACTH (normalized to the +1 charge state) in UV QqTOF, UV linear TOF, and mid-IR linear TOF are 22%, 67%, and 267% respectively.

All patents, patent publications, and other published references mentioned herein are hereby incorporated by reference in their entireties as if each had been individually and specifically incorporated by reference herein. By their citation of various references in this document, applicants do not admit that any particular reference is "prior art" to their invention.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined with reference to the appended claims along with their full scope of equivalents.

What is claimed is:

1. A method for laser desorption ionization of an analyte, the method comprising:
    irradiating the analyte in the presence of energy absorbing molecules at a mid-IR wavelength, wherein the mid-IR wavelength is offset from the IR absorption maximum of the energy absorbing molecules, wherein the irradiation of the analyte at the mid-IR wavelength produces analyte gas phase ions, and wherein a preponderance of the ions for at least one given mass has higher order charge states.

2. The method of claim 1, wherein the analyte is within a matrix of said energy absorbing molecules.

3. The method of claim 1, wherein the energy absorbing molecules comprise photoactive components of a SEND surface upon which the analyte is disposed.

4. The method of claim 1, wherein said mid-IR wavelength is produced by a fixed wavelength laser.

5. The method of claim 1, wherein said mid-IR wavelength is produced by a tunable laser.

6. The method of claim 5, wherein the laser is a tunable optical parametric oscillator (OPO) infrared laser.

7. The method of claim 1, further comprising the step of:
    detecting at least one of said higher order charge state gas phase ions.

8. The method of claim 7, wherein said detecting is performed using a device selected from the group consisting of: ion mobility spectrometer, total ion current measuring device, and mass spectrometer.

9. The method of claim 7, wherein said detecting step is performed using a mass spectrometer.

10. The method of claim 9, wherein said detecting step comprises a mass spectral analysis method using the mass spectrometer.

11. The method of claim 9, wherein said mass spectrometer is a tandem mass spectrometer and said detecting step comprises a tandem mass spectral analysis method using the tandem mass spectrometer.

12. The method of claim 11, wherein said tandem mass spectrometer is selected from the group consisting of QqTOF mass spectrometer, triple quadrupole mass spectrometer, ion trap mass spectrometer, ion trap time-of-flight (TOF) mass spectrometer, ion cyclotron resonance (ICR) mass spectrometer, time-of-flight time-of-flight (TOF-TOF) mass spectrometer, Fourier transform ion cyclotron resonance mass spectrometer, electric sector-magnetic sector mass spectrometer, magnetic sector-electric sector mass spectrometer, and electric sector-electric sector mass spectrometer.

13. The method of claim 11, wherein said tandem mass spectrometer is a QqTOF mass spectrometer.

14. The method of claim 11, wherein said tandem mass spectral analysis method comprises the steps of:
    selecting at least one of the analyte gas phase ions;
    fragmenting at least one of the selected analyte ions into a plurality of product ions; and
    performing a mass spectral analysis method on at least one of said product ions.

15. The method of claim 14, wherein at least one of the selected analyte ions has a mass greater than about 5000 daltons.

16. The method of claim 15, wherein at least one of the selected analyte ions has a mass greater than about 10,000 daltons.

17. The method of claim 16, wherein at least one of the selected analyte ions has a mass greater than about 15,000 daltons.

18. The method of claim 17, wherein at least one of the selected analyte ions has a mass greater than about 25,000 daltons.

19. The method of claim 14, wherein said fragmenting is performed by collision induced dissociation.

20. The method of claim 14, wherein said mass spectral analysis method comprises performing a product ion scan of at least one of said product ions.

21. The method of claim 1, further comprising the antecedent step of:
adsorbing said analyte from an inhomogeneous sample directly onto a SELDI probe.

22. The method of claim 21, wherein said SELDI probe is a SEND probe.

23. The method of claim 21, further comprising the step of:
contacting said probe-adsorbed analyte with the energy absorbing molecules.

24. The method of claim 1, wherein said analyte comprises at least one protein.

25. The method of 24, further comprising the step of:
determining at least a portion of the amino acid sequence of at least one of the protein analytes based on at least one of the analyte gas phase ions.

26. The method of claim 25, wherein said determination step comprises:
performing a product ion scan of at least one of the analyte gas phase ions; and
calculating a plurality of differences in masses among product ions represented in the product ion scan.

27. The method of claim 25, further comprising the steps of:
querying a database with at least a portion of the amino acid sequence for at least one of the protein analytes.

28. The method of claim 24, further comprising the steps of:
performing a product ion scan of at least one of the protein analytes based on at least one of the analyte gas phase ions; and
comparing the product ion scan to at least one predicted product ion scan based on protein or nucleic acid sequence databases,
whereby similarity between the performed product ion scan and at least one of the predicted product ion scans identifies at least one of said protein analytes.

* * * * *